(12) United States Patent
Nelson et al.

(10) Patent No.: US 10,082,504 B2
(45) Date of Patent: Sep. 25, 2018

(54) APPARATUSES AND METHODS FOR GENERATING AND MEASURING ENVIRONMENTAL LEVELS OF ALLERGENS

(71) Applicant: NESTEC SA, Vevey (CH)

(72) Inventors: Richard Nelson, St. Louis, MO (US); Ebenzer Satyaraj, Wildwood, MO (US)

(73) Assignee: Nestec S.A., Vevey (CH)

( * ) Notice: Subject to any disclaimer, the term of this patent is extended or adjusted under 35 U.S.C. 154(b) by 416 days.

(21) Appl. No.: 14/943,623

(22) Filed: Nov. 17, 2015

(65) Prior Publication Data

US 2016/0146808 A1 May 26, 2016

Related U.S. Application Data

(60) Provisional application No. 62/083,647, filed on Nov. 24, 2014.

(51) Int. Cl.
*A61G 10/00* (2006.01)
*G01N 33/566* (2006.01)
(Continued)

(52) U.S. Cl.
CPC ............ *G01N 33/566* (2013.01); *A61B 5/411* (2013.01); *A61B 5/6889* (2013.01); *A61G 10/02* (2013.01);
(Continued)

(58) Field of Classification Search
None
See application file for complete search history.

(56) References Cited

U.S. PATENT DOCUMENTS

| 2004/0005251 A1* | 1/2004 | Branham | A61L 9/20 |
| | | | 422/186.3 |
| 2004/0054262 A1* | 3/2004 | Horak | A61B 5/00 |
| | | | 600/300 |

(Continued)

FOREIGN PATENT DOCUMENTS

WO 20070140601 A1 12/2007

OTHER PUBLICATIONS

Karlsson, A.S. et al., "Evaluation of Petri dish sampling for assessment of cat allergen in airborne dust", Allergy, vol. 57, Jan. 1, 2002, pp. 164-168.

(Continued)

*Primary Examiner* — Erik B Crawford
(74) *Attorney, Agent, or Firm* — Ronald A. Burchett; Julie M. Lappin

(57) ABSTRACT

The present disclosure provides an apparatus comprising an air circulating device, an allergen source comprising an allergen, and a housing. The housing can be collapsible, portable, disposable and configurable. The present disclosure also provides a method comprising positioning an allergen source comprising an allergen in a chamber, distributing at least a portion of the allergen from the allergen source within the chamber, and collecting at least a portion of the distributed allergen. In an embodiment, the level of the shed allergen can be used to measure the effectiveness of various measures implemented to reduce airborne Fel d1 that is emitted from soiled cat litter. In another embodiment, the allergen can be introduced at a desired level in the chamber, and the resultant symptoms of a subject (e.g. a human) within the chamber can be identified and correlated with the amount of allergen.

14 Claims, 3 Drawing Sheets

(51) Int. Cl.
*A61B 5/00* (2006.01)
*A61G 10/02* (2006.01)
*G01N 33/68* (2006.01)

(52) U.S. Cl.
CPC ......... *G01N 33/68* (2013.01); *G01N 2333/24* (2013.01); *G01N 2333/46* (2013.01)

(56) References Cited

U.S. PATENT DOCUMENTS

2009/0145466 A1* 6/2009 Fujita ................... A61G 10/00
                                                        134/95.2
2012/0316402 A1* 12/2012 Salapatek ................. E04H 3/08
                                                        600/300

OTHER PUBLICATIONS

Ronborg, S.M. et al., "Exposure chamber for allergen challenge the development and validation of a new concept," Allergy, vol. 51, No. 2, Feb. 1, 1996, pp. 82-88.
Zahradnik, Eva et al. "Animal Allergens and Their Presence in the Environment", Frontiers in Immunology, vol. 5, Jan. 1, 2014.
International Search Report and Written Opinion PCT/IB2015/058902 dated Jul. 4, 2016.

* cited by examiner

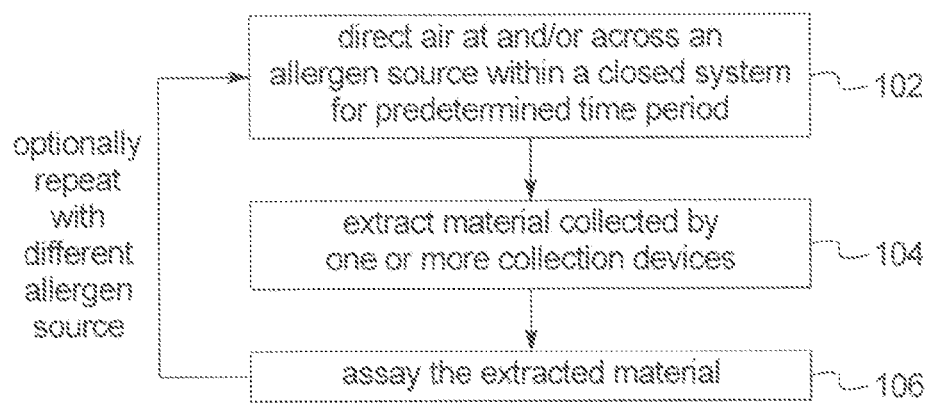
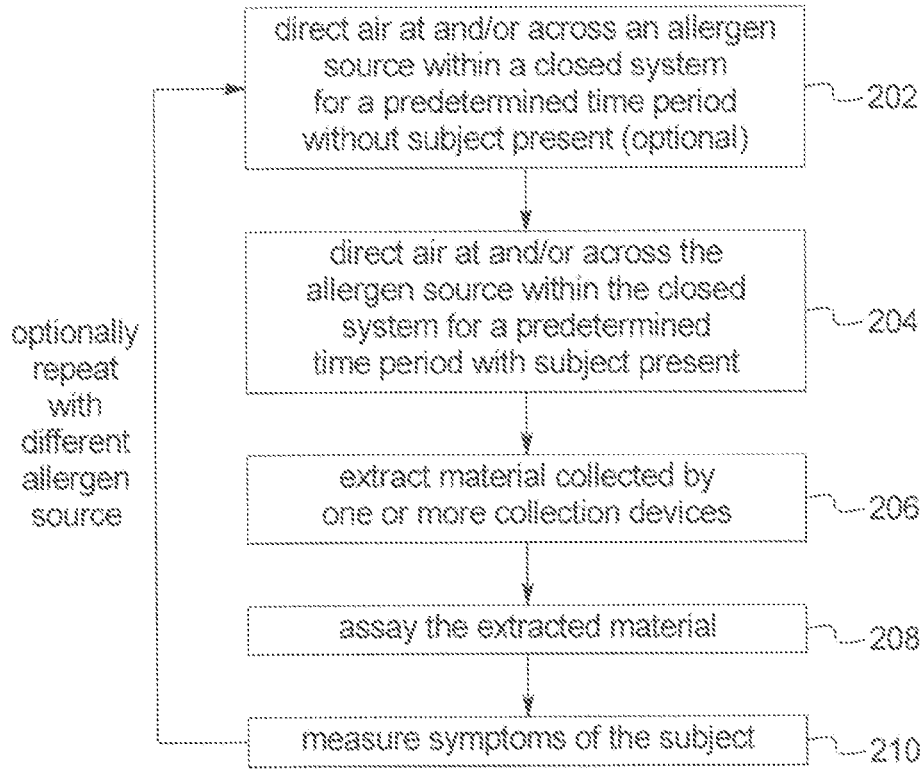

APPARATUSES AND METHODS FOR GENERATING AND MEASURING ENVIRONMENTAL LEVELS OF ALLERGENS

CROSS REFERENCE TO RELATED APPLICATIONS

This application claims priority to U.S. Provisional Application No. 62/083,647 filed Nov. 24, 2014, the disclosure of which is incorporated herein by this reference.

BACKGROUND

Allergy can be defined as a state of immune responsiveness in an animal to an exogenous antigen (or allergen) that is not otherwise harmful to the animal.

Environmental allergens include allergens that derive from organisms such as plants, molds, animals, and insects. Examples of environmental allergens include plant pollens, and mold spores. Other environmental allergens are found in the excretions of furred animals, and insects, such as mites and cockroaches.

Environmental allergens pose a health threat to people of all ages, most particularly children. The presence of such allergens in the environment can result in symptoms or responses that range from mild rhinitis, to skin problems (e.g., itching and hives), asthma, acute respiratory distress, and even to life-threatening anaphylactic reactions. Most cat allergies are caused by a small stable glycoprotein called Fel d1 (*Feline domesticus* allergen number 1). Cat allergens such as Fel d1 can be released from the litter box into the surrounding area. For example, cats often scratch and shift the cat litter, creating dust by which the cat allergens become airborne in the surrounding area. Similarly, scooping the cat litter can circulate cat allergens into the air.

Fel d1 can be particularly problematic because it is lightweight (35 kDa) and thus remains suspended in the air for an extended amount of time. Furthermore, Fel d1 is a sticky protein and consequently adheres to articles within the area surrounding the litter box, such as carpets, walls, furniture, clothing, and curtains, thereby making this allergen difficult to remove after it has circulated from the litter box.

To the inventors' best knowledge, at this time there is no known method for loading an environmental space and quantitatively measuring Fel d1 that is emitted into the environment from soiled cat litter.

SUMMARY

The present disclosure is directed to a chamber that can be loaded with an allergen shed from an allergen source, e.g. cat litter, and the level of the shed allergen in the chamber can be quantitated. In an embodiment, the level of the shed allergen can be used to measure the effectiveness of various measures implemented to reduce airborne Fel d1 that is emitted from the allergen source, e.g. soiled cat litter. In another embodiment, the allergen can be introduced at a desired level, and the resultant symptoms of a subject (e.g. a human) within the chamber can be identified and correlated with the amount of allergen.

Accordingly, in a general embodiment, the present disclosure provides a method comprising: positioning a first allergen source comprising an allergen in a chamber; distributing at least a portion of the allergen from the first allergen source within the chamber; and collecting at least a portion of the distributed allergen.

In an embodiment, the allergen is *Feline domesticus* allergen number 1.

In an embodiment, the method comprises transporting the chamber to a different location at which a second allergen source is used in the chamber.

In an embodiment, the chamber is in a first configuration during the positioning of the allergen source, the distributing of the allergen, and the collecting of the allergen, and the method comprises arranging the chamber in a second configuration that has a size smaller than the first configuration.

In an embodiment, the method comprises measuring the amount of the collected allergen by performing an assay on the collected allergen.

In an embodiment, an individual is present in the chamber during or after the distributing of the allergen, and the method comprises measuring symptoms of the individual.

In an embodiment, the distributing of the allergen comprises maintaining at least a portion of the allergen in suspension in the chamber.

In an embodiment, the distributing of the allergen comprises circulating air in the chamber using a first fan. The distributing of the allergen can comprise circulating air in the chamber using a second fan positioned on an opposite side of the allergen source relative to the first fan. The second fan can be an oscillating fan.

In an embodiment, the distributing of the allergen is performed for a predetermined time period.

In an embodiment, the allergen source comprises a predetermined amount of the allergen when positioned in the chamber.

In another embodiment, the present disclosure provides an apparatus comprising: an air circulating device; an allergen source comprising an allergen; and a housing configured to be selectively arranged in a first configuration that accommodates a human therein and encloses the air circulating device and the allergen source and in a second configuration that is a smaller size than the first configuration.

In an embodiment, the first configuration of the housing forms a closed system such that the allergen does not exit the housing and additional allergen does not enter the housing.

In an embodiment, the apparatus comprises a collecting device configured to collect the allergen.

In an embodiment, the housing comprises a shell made of a flexible non-porous material.

In an embodiment, the housing comprises a collapsible frame.

In another embodiment, the present disclosure provides a method comprising: performing a first test comprising positioning a first allergen source comprising a first amount of an allergen in a first chamber, distributing at least a portion of the first amount of the allergen within the first chamber, and collecting at least a portion of the distributed allergen as a first sample; and performing a second test comprising positioning a second allergen source comprising a second amount of the allergen in a second chamber, distributing at least a portion of the second amount of the allergen within the second chamber, and collecting at least a portion of the distributed allergen as a second sample. The second amount can be the same, larger, or smaller relative to the first amount.

In an embodiment, the first chamber and the second chamber are the same chamber, and the method comprises cleaning a non-porous flexible shell of the chamber between the first test and the second test.

In an embodiment, the first chamber and the second chamber are different chambers, and the first chamber and the second chamber are positioned next to each other while the first and second tests are contemporaneously performed.

In another embodiment, a method of quantitatively determining a cat litter or a diet that produces lower allergen emission to an environment can comprising performing a first test comprising positioning a first allergen source comprising a first amount of an allergen in a first chamber, distributing at least a portion of the first amount of the allergen within the first chamber, and collecting at least a portion of the distributed allergen as a first sample; measuring the amount of allergen in the first sample; performing a second test comprising positioning a second allergen source comprising a second amount of the allergen in a second chamber, distributing at least a portion of the second amount of the allergen within the second chamber, and collecting at least a portion of the distributed allergen as a second sample; measuring the amount of allergen in the second sample; and comparing the amount of allergen in the first sample to the amount of allergen in the second sample to determine whether the first sample or the second sample has lower allergens, where the first allergen source is a first cat litter or first fecal matter from a cat having been fed a first diet and wherein the second allergen source is a second cat litter or a second fecal matter from the cat having been fed a second diet. An advantage of the present disclosure is to provide an apparatus that generates and measures environmental levels of an allergen from a companion animal such as a cat, for example Fel d1.

Another advantage of the present disclosure is to provide a method of generating and measuring environmental levels of an allergen from a companion animal such as a cat, for example Fel d1.

A further advantage of the present disclosure is to measure the effectiveness of various approaches implemented to reduce environmental levels of an airborne allergen that is emitted from an allergen source, e.g. soiled cat litter (that contains Fel d1), such as different types of cat litter and different cat diets.

Another advantage of the present disclosure is to provide a low cost, highly adaptable structure that allows for an allergen to be introduced at a known level at which the effect on a human is studied.

A further advantage of the present disclosure is to perform experimentation in a 100% controlled environment room at less cost than known devices and methods.

Still another advantage of the present disclosure is to expose subjects to certain levels of an allergen of interest to evaluate their symptoms in response to the levels of the allergen.

Yet another advantage of the present disclosure is to provide an apparatus that can be set up at any location.

Another advantage of the present disclosure is to measure environmental levels of an allergen without using an expensive bubble chamber.

A further advantage of the present disclosure is to determine how pet nutrition can decrease allergen production.

Still another advantage of the present disclosure is to determine the extent that various cat litters emit cat allergens such as Fel d1.

Yet another advantage of the present disclosure is to provide a disposable, portable, collapsible and easily cleaned chamber for measuring environmental levels of an allergen.

Another advantage of the present disclosure is to suspend and/or distribute particles so that an environmental level of an allergen associated with the particles can be measured.

Still another advantage of the present disclosure is to measure environmental levels of an allergen without using a large amount of space.

Yet another advantage of the present disclosure is to measure environmental levels of an allergen using a chamber that is configurable, for example with respect to negative pressure, positive pressure, or ambient pressure.

Another advantage of the present disclosure is to measure environmental levels of an allergen in a closed system.

Additional features and advantages are described herein and will be apparent from the following Detailed Description and the Figures.

BRIEF DESCRIPTION OF THE FIGURES

FIG. 3 shows a flowchart of an embodiment of a method provided by the present disclosure.

FIG. 4 shows a flowchart of an embodiment of a method provided by the present disclosure.

DETAILED DESCRIPTION

Figure 1:
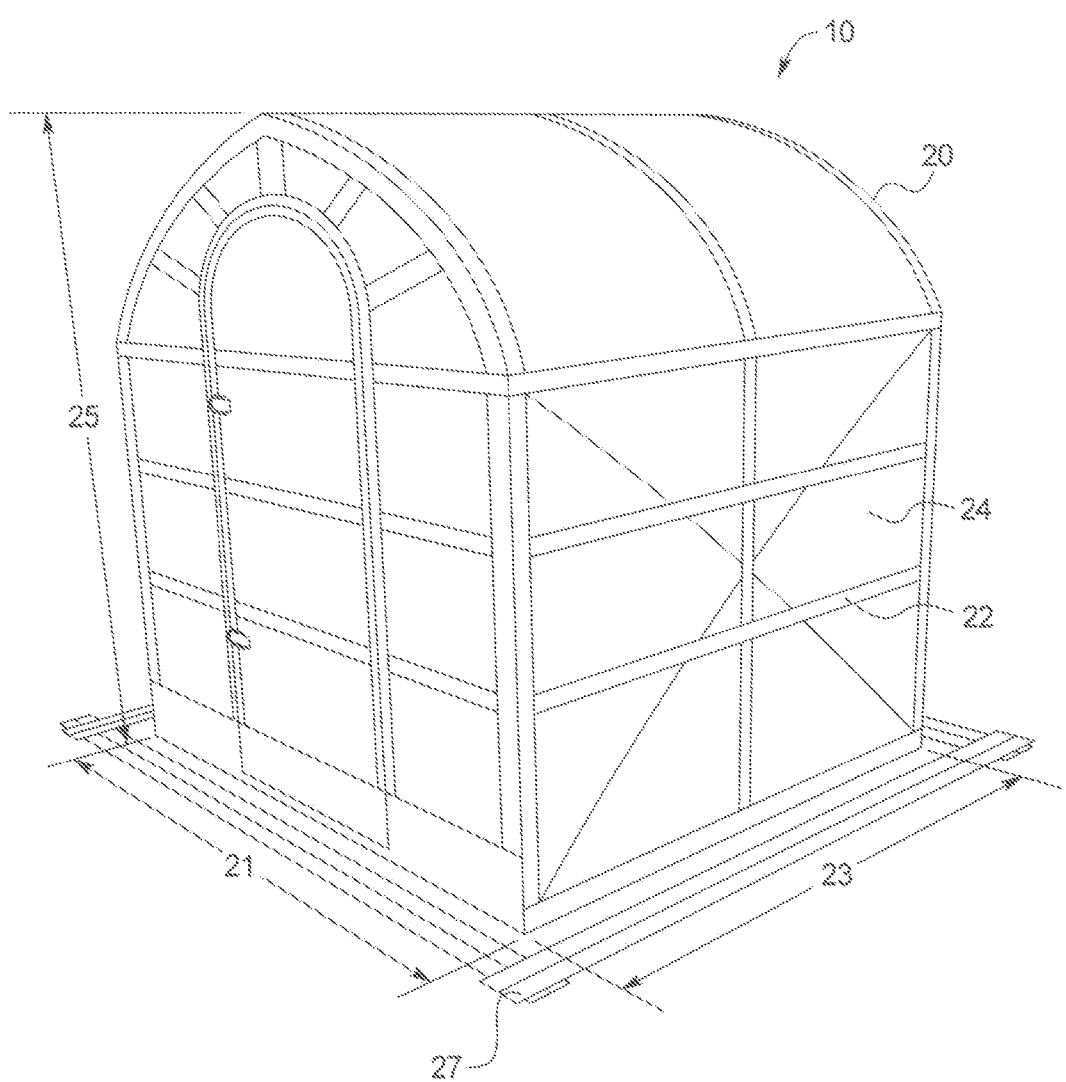
FIG. 1 shows a perspective view of an embodiment of an apparatus provided by the present disclosure.

As used in this disclosure and the appended claims, the singular forms "a," "an" and "the" include plural referents unless the context clearly dictates otherwise. The words "comprise," "comprises" and "comprising" are to be interpreted inclusively rather than exclusively. Likewise, the terms "include," "including" and "or" should all be construed to be inclusive, unless such a construction is clearly prohibited from the context. However, the devices disclosed herein may lack any element that is not specifically disclosed. Thus, a disclosure of an embodiment using the term "comprising" includes a disclosure of embodiments "consisting essentially of" and "consisting of" the components identified.

The term "pet" means any animal which can produce and/or carry an allergen. The pet can be an avian, bovine, canine, equine, feline, hicrine, lupine, murine, ovine, or porcine animal. The pet can be any suitable animal, and the present disclosure is not limited to a specific pet animal. The term "companion animal" means a dog or a cat.

While the terms "individual," "subject" and "patient" are often used herein to refer to a human, the present disclosure is not so limited. Accordingly, these terms refer to any animal, mammal or human.

Ranges are used herein in shorthand to avoid listing every value within the range. Any appropriate value within the range can be selected as the upper value or lower value of the range. Moreover, the numerical ranges herein include all integers, whole or fractions, within the range.

All percentages expressed herein are by weight of the total weight of the food composition unless expressed otherwise. When reference is made to the pH, values correspond to pH measured at 25° C. with standard equipment. As used herein, "about" or "substantially" in reference to a number is understood to refer to numbers in a range of numerals, for example the range of −10% to +10%, −5% to +5%, −1% to +1%, and in one aspect −0.1% to +0.1% of the referenced number.

The methods and devices and other advances disclosed herein are not limited to particular methodologies, protocols, and reagents because, as the skilled artisan will appreciate, they may vary. Further, the terminology used herein is for the purpose of describing particular embodiments only and does not limit the scope of that which is disclosed or claimed.

Unless defined otherwise, all technical and scientific terms, terms of art, and acronyms used herein have the meanings commonly understood by one of ordinary skill in the art in the field(s) of the present disclosure or in the field(s) where the term is used. Although any compositions, methods, articles of manufacture, or other means or materials similar or equivalent to those described herein can be used, specific devices, methods, articles of manufacture, or other means or materials are described herein.

The present disclosure relates generally to apparatuses and methods for generating and measuring environmental levels of an allergen, for example an allergen from a companion animal such as a cat. More specifically, the present disclosure is directed to a chamber that can be loaded with an allergen emitted from cat litter, and the level of the emitted allergen in the chamber can be quantitated.

Figure 2:
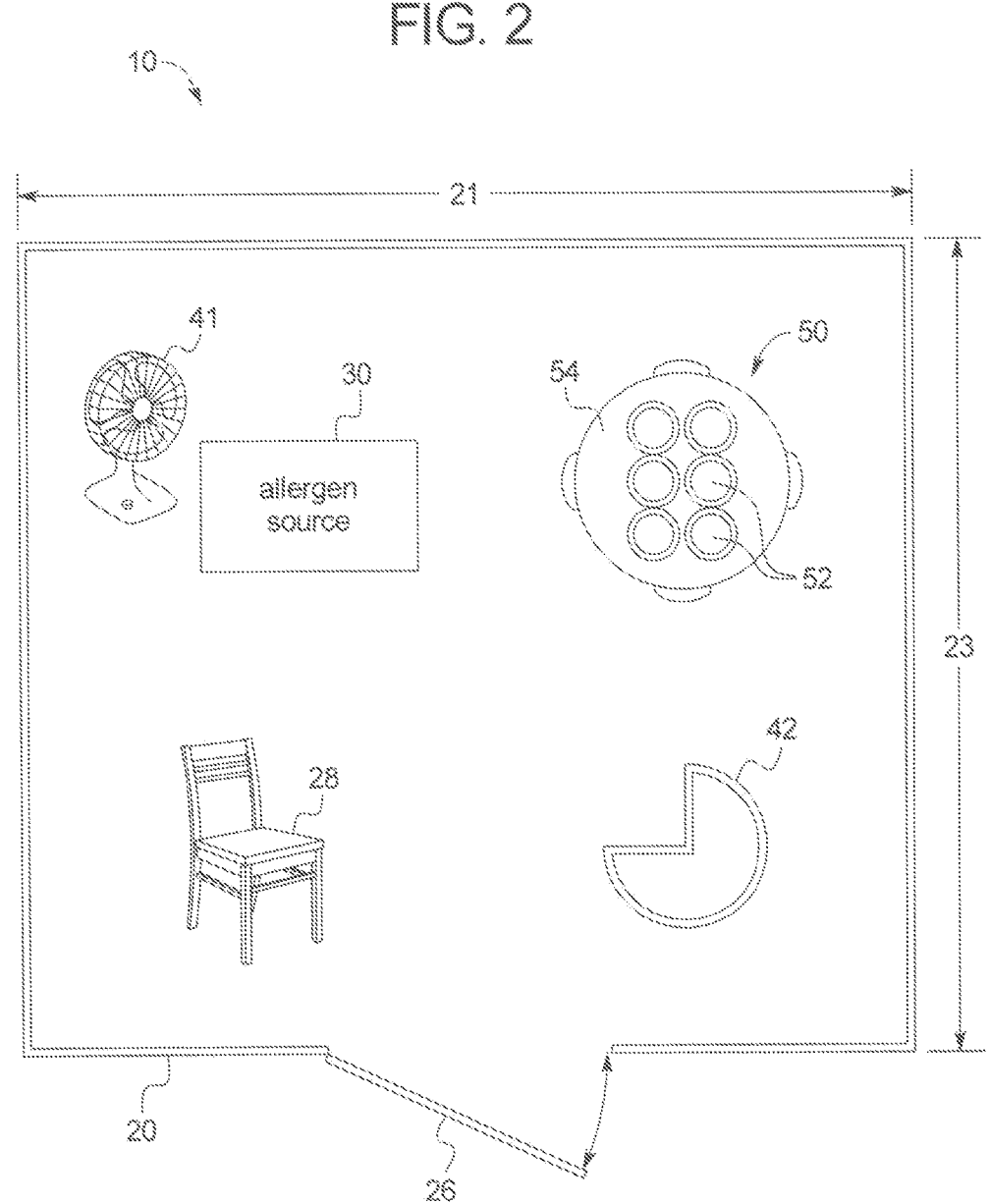
FIG. 2 shows a schematic diagram of an embodiment of an apparatus provided by the present disclosure.

FIGS. 1 and 2 generally illustrate an embodiment of an apparatus 10 provided by the present disclosure. The apparatus 10 can generate and can measure environmental levels of an allergen as discussed in detail hereafter. The apparatus 10 can comprise a housing 20, an allergen source 30, and an air circulation device 41. The housing 20 can be portable; in an embodiment, the housing 20 is a collapsible tent. As used herein, a "collapsible" article is capable of being configured into a smaller size without causing damage to the article, and in one aspect, without the need for tools.

The housing 20 can form a chamber. Although the housing 20 can be air-tight, the housing 20 does not have to be air-tight, and an embodiment of the housing 20 merely forms a closed system such that the tested allergen does not exit the interior of the housing 20 during use of the apparatus 10 and additional allergen does not enter the interior of the housing 20 during use of the apparatus 10.

As shown in FIG. 1, the housing 20 can comprise a frame 22 that supports a shell 24 to form the chamber. In an embodiment, the frame 22 is made of a metal material. In one aspect, the shell 24 can be made of non-porous material. The shell 24 can define the interior of the housing 20. For example, the shell 24 can form a majority of the outer surface of the housing 20 (e.g. substantially all of the outer surface of the housing 20) and/or a majority of the inner surface of the housing 20 (e.g. substantially all of the inner surface of the housing 20).

In one embodiment, at least a portion of the housing 20 can be folded to enable transportation and compact storage. For example, at least a portion of the frame 22 and/or at least a portion of the shell 24 can be folded to enable transportation and compact storage of the housing 20. The housing 20 can be arranged in (i) an operative configuration in which the housing 20 defines an interior and (ii) a storage/transport configuration in which the housing 20 defines an interior that is smaller relative to the operative configuration or in which the housing 20 does not define an interior e.g. the housing 20 is folded completely upon itself. For example, the frame 22 can comprise one or more poles that can be configured in (i) an operative configuration in which the poles are inserted into each other at their ends to form a substantially rigid and/or stable arrangement and (ii) a storage/transport configuration in which the poles are in a compact arrangement, such as laying side-by-side with each other. The poles can be hollow and connected to each other by one or more cords, such as rubber ropes, that pass through the interiors of the poles to enable a user to move the housing 20 between configurations and arrange the housing 20 in the desired configuration.

The shell 24 can be flexible; for example, the shell 24 can comprise a fabric such as polyester, a plastic such as flexible polyvinyl, and/or linoleum. In one embodiment, the shell can include a water impermeable polymer. Such a polymer can act as the shell, be laminated to the shell, or otherwise be affixed or coated to the shell. The shell 24 can be made of a material that can be easily cleaned, for example with isopropyl or ethanol solutions, such that no measurable allergen remains in the housing 20 after cleaning. In an embodiment, the housing 20 is at least partially disposable; for example, the frame 22 and/or the shell 24 can be disposable. As used herein, a "disposable" article is designed for a single use after which it is recycled or is disposed as solid waste. For example, a disposable article is not permanently fixed in position in a building, and a disposable article can be moved from its position without damaging the article.

The shell 24 can be connected to the frame 22 to form the housing 20. For example, a portion of the shell 24 can be reversibly attachable to and removable from the frame 22. Alternatively or additionally, a portion of the shell 24 can be fixedly attached to and/or integral with the frame 22. The shell 24 can comprise a door 26 that opens and closes, for example by a zipper. The bottom of the shell 24 can be secured to a solid surface, for example by floor tape 27. In an embodiment, the shell 24 does not have an integrated floor; additionally or alternatively, a portion of the shell 24 can comprise an integrated floor. If the bottom of the shell 24 is secured to a solid surface, in one aspect, the solid surface does not have carpet.

Referring again to FIGS. 1 and 2, the housing 20 in the operative configuration can have any size, and in one aspect, at least large enough to contain a human seated on a chair or stool 28. The housing 20 in the operative configuration can have a width 21. As non-limiting examples, the width 21 can be at least three feet, at least four feet, at least five feet, or in one aspect, at least six feet, and/or the width 21 can be at most nine feet, at most eight feet, and in one aspect, at most seven feet. In an embodiment, the width 21 can be about six feet, but the housing 20 in the operative configuration is not limited to a specific distance of the width 21.

The housing 20 in the operative configuration can have a depth 23 perpendicular to the width 21. As non-limiting examples, the depth 23 can be at least three feet, at least four feet, at least five feet, and in one aspect, at least six feet, and/or the depth 23 can be at most nine feet, at most eight feet, and in one aspect, at most seven feet. In an embodiment, the depth 23 can be about six feet, but the housing 20 in the operative configuration is not limited to a specific distance of the depth 23.

As shown in FIG. 1, the housing 20 in the operative configuration can have a height 25. As non-limiting examples, the height 25 can be at least four feet, at least five feet, and in one aspect, at least six feet, and/or the height 25 can be at most ten feet, at most nine feet, and in one aspect, at most eight feet. In an embodiment, the height 25 can be about seven feet, but the housing 20 in the operative configuration is not limited to a specific distance of the height 25. In one embodiment, the width 21 can be substantially the same for the majority of the height 25 of the housing 20 and/or the depth 23 can be substantially the same for the majority of the height 25 of the housing 20, although the housing 20 can taper at the top end thereof in a non-limiting embodiment shown in FIG. 1.

As noted above, the housing 20 in the transport/storage configuration defines an interior that is smaller relative to the operative configuration or does not define an interior e.g. the housing 20 can be folded completely upon itself. For example, at least one of the width 21, the depth 23 or the height 25 can be less in the transport/storage configuration than the operative configuration, and in one aspect, all three can be less in the transport/storage configuration than the operative configuration. In an embodiment, the housing 20 in the transport/storage configuration can be positioned within and carried by a conventional backpack.

Referring to FIG. 2, the allergen source 30 can be positioned within the housing 20. The allergen source 30 can be any source of an allergen, including an allergen from a pet, in one aspect, from a companion animal, and in one specific aspect, from a cat. For example, the allergen source 30 can be a cat litter box that contains cat litter soiled by urine and/or feces. As another example, the allergen source 30 can be an open container in which cat hair is positioned. An "allergen" is any substance that can produce an immune response in some individuals but would otherwise be harmless to such individuals.

The air circulation device 41 can be positioned within the housing 20. The air circulation device 41 can be any device that suspends and/or distributes at least a portion of the allergen from the allergen source 30. For example, the air circulation device 41 can be at least one mechanical fan comprising a rotating arrangement of vanes or blades that extend from a hub. In a one embodiment, the air circulation device 41 can comprise a primary fan, and the apparatus 10 can comprise an additional air circulation device 42 that can comprise a secondary fan such as an oscillating fan. An "oscillating fan" is a fan for which the hub rotates on at least two axes, namely the axis of rotation of the vanes/blades and another axis that is different than the axis of rotation of the vanes/blades. In one embodiment, the other axis of the oscillating fan can be perpendicular to the axis of rotation of the vanes/blades.

The air circulation device 41 and the additional air circulation device 42 can direct air to circulate the allergen from the allergen source 30 into the environment of the interior of the housing 20. For example, the air circulation device 41 can be positioned to blow or otherwise direct air at and/or across the allergen source 30, and the additional air circulation device 42 can be positioned on the directly opposite side of the allergen source 30 from the air circulation device 41 to blow or otherwise direct air in the opposite direction and thus produce air turbulence adjacent to and/or above the allergen source 30. This air turbulence can maintain particles from the allergen source 30 in suspension in the environment of the interior of the housing 20 during testing. For example, in an embodiment where the allergen source 30 comprises a cat litter box, the air turbulence from the air circulation device 41 and the additional air circulation device 42 can distribute and/or suspend the allergen including cat litter particles or fine dust containing the allergen in the interior of the housing 20.

The apparatus 10 can comprise a collection device 50 that can be positioned within the housing 20. The collection device 50 can be any device capable of collecting the allergen and/or particles comprising the allergen. In one embodiment, the collection device 50 comprises one or more petri plates 52. As a non-limiting example, the one or more petri plates 52 can comprise 10 cm petri plates pre-coated with a 2% gelatin solution from cold water fish skin. The one or more petri plates 52 can be positioned adjacent to each other or in different locations in the housing 20. As a non-limiting example, some of the petri plates 52 can be positioned on the floor approximately 10 cm from the edge of the allergen source 30, and some of the petri plates 52 can be positioned on a table 54, such as a 1$m$ table approximately 1 m from the allergen source 30.

The air circulation device 41 and the additional air circulation device 42 can be activated for a predetermined time period, and the material collected by the collection apparatus 50 can be extracted after the predetermined time period. The collected material can be extracted using any compound capable of removing the allergen from the collection device 50, for example a solution of phosphate buffered saline, 0.1% polysorbate 20 such as TWEEN® 20, and 0.15% antimicrobial such as KATHON® ("PBS-Tk").

Then the material extracted from the collection device 50 can be assayed to determine the quantity of allergen emitted from the allergen source 30 during the predetermined time period. In an embodiment, the extracted material can be assayed to determine the quantity of Fel d1 emitted from a soiled cat litter box during a predetermined time period. For example, the extracted material can be assayed for Fel d1 using a commercially available Fel d1 enzyme-linked immunosorbent assay (ELISA) kit such as Product Code EL-FD1 from Indoor Biotechnologies. The allergen can be quantitated as ng/plate/hour.

As discussed in further detail in Example 1 later in this application, the present inventors have verified the effectiveness of the apparatus 10. For example, two soiled litter boxes from the same cat were used for different amounts of time (in days). The longer the cat had used the litter box (allergen source 30), the higher the level of Fel d1 that was emitted into the housing 20 by the litter box (allergen source 30), collected by the collection device 50, and quantitated by assay.

In one example, the apparatus 10 can be configurable. For example, one or more of the allergen source 30, the air circulation device 41, the additional air circulation device 42, or the collection device 50 can be movable relative to the housing 20, e.g. not fixedly attached to the housing 20. As another example, the shell 24 can comprise portals for sampling or injecting allergen, e.g. at least a portion of the allergen source 30 can be positioned exterior relative to the housing 20, and/or at least a portion of the collection device 50 can be positioned exterior relative to the housing 20. As yet another example, a pipe can be attached to and/or inserted through the shell 24. The pipe can be used to establish and/or maintain a desired pressure in the interior of the housing 20, for example a positive pressure, a negative pressure, or an ambient pressure. If a pipe is used, in one aspect, the apparatus 10 can still provide the closed system in which the tested allergen does not exit the interior of the housing 20 during use of the apparatus 10 and additional allergen does not enter the interior of the housing 20 during use of the apparatus 10.

Another aspect of the present disclosure includes a method 100 of generating and measuring environmental levels of an allergen, for example an allergen from a companion animal such as a cat. An embodiment of the method 100 is generally illustrated in FIG. 3. The method 100 can employ the apparatus 10 and/or another apparatus.

In Step 102, air can be directed at and/or across a first allergen source that is contained within a chamber that provides a closed system. The chamber can contain one or more collection devices. Additionally or alternatively, one or more collection devices can be outside of the chamber but have access to the interior of the chamber through one or more portals. Step 102 can be performed for a predetermined time period.

One or more air circulation devices, positioned within the chamber, can direct the air at and/or across the first allergen source during Step 102. The one or more air circulation devices can be any device capable or suspending and/or distributing the allergen in the chamber. In one embodiment, a primary fan can be positioned to blow or otherwise direct air at and/or across the first allergen source. A secondary oscillating fan can be positioned on the directly opposite side of the first allergen source from the primary fan to blow or otherwise direct air in the opposite direction and thus produce air turbulence adjacent to and/or above the first allergen source. This air turbulence can maintain particles from the first allergen source in suspension in the environment of the interior of the housing during testing.

In Step 104, material collected by the one or more collection devices can be extracted, for example after Step 102 is completed. Each of the one or more collection devices can be any device capable of collecting the allergen and/or particles comprising the allergen. For example, the one or more collection devices can comprise petri plates at various positions within the chamber. The material can be extracted using any compound capable of removing the allergen from the one or more collection devices, for example a phosphate-buffered solution.

In Step 106, the extracted material can be assayed to determine the quantity of the allergen collected by the one or more collection devices. Any assay capable of identifying a quantity of the allergen can be used, for example an ELISA kit. The quantity of the allergen collected by the one or more collection devices during the test can be indicative of the quantity of allergen emitted by the allergen source during the test.

In an embodiment, the method 100 can measure the effectiveness of various approaches implemented to reduce environmental levels of an airborne allergen. In such an embodiment, the method 100 can be repeated with a second allergen source that is different than the first allergen source. In such an embodiment, Steps 102, 104 and 106 can be performed the same as they were previously performed, other than the different allergen sources.

In one example, the first allergen source can be a first cat litter box containing a first type of cat litter, and the second allergen source can be a second cat litter box containing a second type of cat litter. Other than the different types of cat litter, the first and second cat litter boxes can be subjected to one or more same or similar conditions, for example one or more of the same location, the same time period of use, the same amount of waste matter deposited therein, use by the same breed of cat, or use by the same specific cat. In this example, the method 100 can determine which of the first and second types of cat litter is more effective at preventing emission of the allergen from the litter box. By using the method 100 to measure which type of cat litter is more effective at preventing emission of the allergen from the litter box, an individual can select a type of cat litter that minimizes or prevents the individual's exposure to the allergen.

As another example, the first allergen source can be a first cat litter box used by a cat that has been provided a first diet, and the second allergen source can be a second cat litter box used by a cat that has been provided a second diet. The cat that has been provided the first diet can be the same breed or the same specific cat as the cat that has been provided the second diet. Other than the different diets of the cat(s), the first and second cat litter boxes can be subjected to one or more same or similar conditions, for example one or more of the same location, the same time period of use, the same amount of waste matter deposited therein, the same type of cat litter, use by the same breed of cat, or use by the same specific cat. In this example, the method 100 can determine which of the first and second diets results in the cat producing less of the allergen relative to the other diet. By using the method 100 to measure which diet is more effective at preventing allergen production, an individual can administer a diet to the cat that minimizes or prevents the individual's exposure to the allergen.

As still another example, the first allergen source can be an allergen source that collected allergen in a first location, such as a first room of a house, and the second allergen source can be an allergen source that collected allergen in a second location different than the first location, such as a second room of the house. Other than the location at which the allergen sources are positioned, the first and second allergen sources can be subjected to one or more same or similar conditions, for example the same time period of use and/or use by the same specific cat. In this example, the method 100 can determine which of the locations contains less of the allergen relative to the other location. By using the method 100 to determine which location contains more allergen, an individual can avoid the location to thereby minimize or prevent exposure to the allergen.

The second allergen source can be used in the same chamber as the first allergen source after the testing of the first allergen source is completed and in one aspect, after the chamber is cleaned. Alternatively, the second allergen source can be used in a different chamber than the first allergen source, for example substantially contemporaneously; the chambers can be, in one aspect, substantially the same, for example the same dimensions and/or the same materials.

In another embodiment, a method 200 can expose a subject, in one aspect, one or more human subjects, to an allergen to evaluate the symptoms of the subject. The method 200 can employ the apparatus 10 and/or another apparatus.

In Step 202, which is optional, the subject can be absent while a chamber that provides a closed system is loaded with an allergen. In one embodiment, the subject can be absent during a predetermined time in which air is directed at and/or across a first allergen source contained within the chamber. For example, the allergen can be distributed in the apparatus for a predetermined time period without the subject, such as thirty-six hours.

The chamber can contain one or more collection devices. Additionally or alternatively, one or more collection devices can be outside of the chamber but have access to the interior of the chamber through one or more portals.

In Step 204, the subject can be present in the chamber that provides a closed system while the allergen is distributed and/or circulated therein. In one embodiment, the subject can be present in the chamber during a predetermined time in which air is directed at and/or across a first allergen source contained within the chamber. In another embodiment, when the chamber is preloaded according to step 202, the subject can be present in the chamber during a predetermined time in which air is circulated. In one aspect, the allergen source can remain in the chamber and, in another aspect, the allergen source can be previously removed from the chamber. The subject can be within the chamber with the allergen circulating for a predetermined time period, such as four to eight hours.

One or more air circulation devices, positioned within the chamber, can direct the air at and/or across the first allergen source during Steps 202 and 204. The one or more air circulation devices can be any device capable or suspending and/or distributing the allergen in the chamber. In an embodiment, a primary fan can be positioned to blow or otherwise direct air at and/or across the first allergen source. A secondary oscillating fan can be positioned on the directly opposite side of the first allergen source from the primary fan to blow or otherwise direct air in the opposite direction and thus produce air turbulence adjacent to and/or above the first allergen source. This air turbulence can maintain particles from the first allergen source in suspension in the environment of the interior of the housing during testing.

In Step 206, material collected by the one or more collection devices can be extracted, for example after Step 204 is completed. Each of the one or more collection devices can be any device capable of collecting the allergen and/or particles comprising the allergen. For example, the one or more collection devices can comprise petri plates at various positions within the chamber. The material can be extracted using any compound capable of removing the allergen from the one or more collection devices, for example a phosphate-buffered solution.

In Step 208, the extracted material can be assayed to determine the quantity of the allergen collected by the one or more collection devices during the test. Any assay capable of identifying a quantity of the allergen can be used, for example an ELISA kit. The quantity of the allergen collected by the one or more collection devices during the test can be indicative of the quantity of allergen emitted by the allergen source during the test.

In Step 210, the symptoms, if any, of the subject in response to the airborne allergen can then be evaluated to determine the sensitivity of the subject to the allergen. The symptoms, if any, of the subject can be correlated to the quantity of the allergen emitted from the allergen source during these test.

The method 200 can measure the symptoms of the subject at various environmental levels of the allergen. In such an embodiment, Steps 202, 204, 206 and 208 can be repeated, for example with the predetermined time period of Step 204 being different, or with a second allergen source different from the first allergen source (subjected to at least one different condition and/or has at least one different characteristic, e.g. the amount of the allergen in the allergen source is different). The method 200 can be used determine a threshold amount of allergen at which symptoms are induced in the subject. In an embodiment of the method 200, a predetermined amount of the allergen can be provided in the allergen source. For example, hair from a cat may be assayed to determine the concentration of the allergen in the hair, and then the hair may be provided in the allergen source in an amount that contains the desired amount of allergen. The predetermined amount of the allergen can be used to determine the symptoms of the subject in response to the predetermined amount, and various predetermined amounts can be used to determine a threshold amount of allergen that must be exceeded to induce the symptoms in the specific subject.

EXAMPLES

By way of example and not limitation, the following non-limiting examples are illustrative of apparatuses and methods of generating and measuring environmental levels of an allergen in embodiments provided by the present disclosure.

Example 1

A first experiment was performed regarding differential loading of environmental chambers using different mass amounts of cat hair from the same cat. Three environmental chambers were loaded with 1, 0.5 or 0.25 g of cat hair from the cat "Montana." Dust was collected using petri plates coated with 0.2% gelatin for 72 hours.

The dust was extracted from the petri plates and analyzed for Fel d1 using a commercially available ELISA kit (Indoor Pharmaceuticals). The level of Fel d1 was then normalized to time (ng Fel d1/plate/hour). Each dust collection was done in triplicate. Results are shown in the table below and show that the amount of allergen source corresponds closely to the level detected in the environmental chamber.

TABLE 1

| grams or hair | Fel d1 Levels in ECs ng Fel d1/plate/hr | SD |
|---|---|---|
| 1.0 g | 0.087 | 0.015 |
| 0.5 g | 0.060 | 0.006 |
| 0.25 g | 0.015 | 0.006 |

Example 2

A second experiment was performed in which three environmental chambers were loaded with 1 g of hair from three different cats, namely high, medium and low level Fel d1-producing cats. The level of Fel d1 for each cat was determined by measuring the Fel d1 in their hair and normalizing to mass amount of hair (ng Fel d1/mg hair). The hair from each cat was measured in triplicate.

Fel d1 levels in the cat hair used to load the environmental chambers are shown in the table below.

TABLE 2

| Cat | ng Fel d1/mg hair |
|---|---|
| Montana | 828 ng/mg hair |
| Stymie | 277 ng/mg hair |
| Koala | 16 ng/mg hair |

The dust was extracted from the petri plates and analyzed for Fel d1 as previously described in Example 1. Results are shown in the table below and show that the allergen production of the cat corresponds closely to the level detected in the environmental chamber.

TABLE 3

| Location | House Fel D1 levels ng Fel d1/plate/hr | SD |
|---|---|---|
| JL | 0.055 | 0.0076 |
| CT CR (cat) | 0.049 | 0.0028 |
| CT BR (no cat) | 0.009 | 0.0086 |

Example 3

A third experiment was performed in which the level of Fel d1 in homes of cat owners was determined by collecting dust using the method described previously in Example 1. Dust was collected in "cat rooms" and "cat-free rooms" when possible in the same household. Dust was collected for 5 days (120 hours). Results are shown in the table below and show that the allergen production of the cat corresponds closely to the level detected in the environmental chamber.

TABLE 4

| Location | House Fel D1 levels ng Fel d1/plate/hr | SD |
|---|---|---|
| JL | 0.055 | 0.0076 |
| CT CR (cat) | 0.049 | 0.0028 |
| CT BR (no cat) | 0.009 | 0.0086 |

It should be understood that various changes and modifications to the embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method comprising:
    positioning a first allergen source comprising an allergen in a chamber;
    distributing at least a portion of the allergen from the first allergen source within the chamber; and
    collecting at least a portion of the distributed allergen;
    wherein the chamber is in a first configuration during the positioning of the allergen source, the distributing of the allergen, and the collecting of the allergen, and the method further comprises arranging the chamber in a second configuration that has a size smaller than the first configuration.

2. The method of claim 1, wherein the allergen is Feline domesticus allergen number 1.

3. The method of claim 1, further comprising measuring the amount of the collected allergen by performing a Fel d1 enzyme-linked immunosorbent assay (ELISA) on the collected allergen.

4. The method of claim 1, wherein an individual is present in the chamber during at least a portion of the distributing of the allergen, and the method further comprises measuring symptoms of the individual.

5. The method of claim 1, wherein the distributing of the allergen comprises maintaining at least a portion of the allergen in suspension in the chamber.

6. The method of claim 1, wherein the distributing of the allergen comprises circulating air in the chamber using a first fan.

7. The method of claim 6, wherein the distributing of the allergen comprises circulating air in the chamber using a second fan positioned on an opposite side of the allergen source relative to the first fan.

8. The method of claim 7, wherein the second fan is an oscillating fan.

9. The method of claim 1, wherein the distributing of the allergen is performed for a predetermined time period.

10. The method of claim 1, wherein the allergen source comprises a predetermined amount of the allergen when positioned in the chamber.

11. A method comprising:
    performing a first test comprising positioning a first allergen source comprising a first amount of an allergen in a first chamber, distributing at least a portion of the first amount of the allergen within the first chamber by circulating air in the first chamber using a first fan and a second fan, the second fan be positioned on an opposite side of the first allergen source relative to the first fan, collecting at least a portion of the distributed allergen as a first sample, and measuring the amount of the collected allergen by performing a Fel d1 enzyme-linked immunosorbent assay (ELISA) on the first sample; and
    performing a second test comprising positioning a second allergen source comprising a second amount of the allergen in a second chamber, distributing at least a portion of the second amount of the allergen within the second chamber by circulating air in the second chamber using a first fan and a second fan, the second fan be positioned on an opposite side of the second allergen source relative to the first fan, collecting at least a portion of the distributed allergen as a second sample, and measuring the amount of the collected allergen by performing the Fel d1 enzyme-linked immunosorbent assay (ELISA) on the second sample.

12. The method of claim 11, wherein the first chamber and the second chamber are the same chamber, and the method further comprises cleaning a non-porous flexible shell of the chamber between the first test and the second test.

13. The method of claim 11, wherein the first chamber and the second chamber are different chambers, and the first chamber and the second chamber are positioned next to each other while the first and second tests are contemporaneously performed.

14. A method of quantitatively determining a cat litter or a diet that produces lower emission of an allergen to an environment, the method comprising:
    performing a first test comprising positioning a first allergen source comprising a first amount of the allergen in a first chamber, distributing at least a portion of the first amount of the allergen within the first chamber, and collecting at least a portion of the distributed allergen as a first sample;
    measuring the amount of the allergen in the first sample;
    performing a second test comprising positioning a second allergen source comprising a second amount of the allergen in a second chamber, distributing at least a portion of the second amount of the allergen within the second chamber, and collecting at least a portion of the distributed allergen as a second sample;
    measuring the amount of the allergen in the second sample; and
    comparing the amount of the allergen in the first sample to the amount of the allergen in the second sample to determine whether the first sample or the second sample has a lower allergen content;
    wherein the first allergen source is a first cat litter, a first hair sample from a cat, or first fecal matter from the cat having been fed a first diet and wherein the second allergen source is a second cat litter, a second hair sample from the cat, or a second fecal matter from the cat having been fed a second diet.

* * * * *

UNITED STATES PATENT AND TRADEMARK OFFICE
CERTIFICATE OF CORRECTION

PATENT NO. : 10,082,504 B2
APPLICATION NO. : 14/943623
DATED : September 25, 2018
INVENTOR(S) : Richard Nelson and Ebenzer Satyaraj Page 1 of 1

It is certified that error appears in the above-identified patent and that said Letters Patent is hereby corrected as shown below:

On the Title Page

Item [72], delete "Ebenzer Satyaraj", and insert --Ebenezer Satyaraj--

Signed and Sealed this
Fifteenth Day of January, 2019

Andrei Iancu
*Director of the United States Patent and Trademark Office*